(12) United States Patent
Park et al.

(10) Patent No.: US 9,011,338 B2
(45) Date of Patent: Apr. 21, 2015

(54) GAP FILLING FOR SPECTRAL DOPPLER ULTRASOUND

(75) Inventors: Mikyoung Park, Issaquah, WA (US); Chi Hyung Seo, Issaquah, WA (US); Paul Donald Freiburger, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 27 days.

(21) Appl. No.: 13/548,103

(22) Filed: Jul. 12, 2012

(65) Prior Publication Data

US 2014/0018683 A1    Jan. 16, 2014

(51) Int. Cl.
*A61B 8/00* (2006.01)
*A61B 8/08* (2006.01)

(52) U.S. Cl.
CPC ............ *A61B 8/5207* (2013.01); *A61B 8/0883* (2013.01); *A61B 8/488* (2013.01)

(58) Field of Classification Search
USPC ................................................ 600/437–469
See application file for complete search history.

(56) References Cited

U.S. PATENT DOCUMENTS

| | | | |
|---|---|---|---|
| 4,559,952 A | 12/1985 | Angelsen et al. | |
| 5,457,717 A | 10/1995 | Bellamy | |
| 5,476,097 A | 12/1995 | Robinson | |
| 5,642,732 A * | 7/1997 | Wang ............................ | 600/453 |
| 5,913,824 A | 6/1999 | Ogasawara et al. | |
| 5,971,923 A * | 10/1999 | Finger ........................... | 600/437 |
| 6,039,692 A | 3/2000 | Kristoffersen | |
| 6,171,244 B1 * | 1/2001 | Finger et al. .................. | 600/437 |
| 6,262,749 B1 * | 7/2001 | Finger et al. .................. | 345/564 |
| 6,300,961 B1 * | 10/2001 | Finger et al. .................. | 345/505 |
| 6,322,505 B1 * | 11/2001 | Hossack et al. ............... | 600/437 |
| 6,352,511 B1 * | 3/2002 | Hossack et al. ............... | 600/443 |
| 6,417,857 B2 * | 7/2002 | Finger et al. .................. | 345/505 |
| 6,450,959 B1 * | 9/2002 | Mo et al. ....................... | 600/441 |
| 6,629,926 B1 * | 10/2003 | Finger et al. .................. | 600/437 |
| 6,824,518 B2 * | 11/2004 | Von Behren et al. ......... | 600/443 |
| 7,128,713 B2 * | 10/2006 | Moehring et al. ............ | 600/453 |
| 7,611,464 B2 * | 11/2009 | Li .................................. | 600/441 |
| 7,981,036 B2 * | 7/2011 | Li .................................. | 600/441 |
| 8,157,735 B2 * | 4/2012 | Shin et al. ..................... | 600/441 |
| 8,206,302 B2 * | 6/2012 | Zhang et al. .................. | 600/453 |
| 2004/0102703 A1 * | 5/2004 | Behren et al. ................. | 600/443 |
| 2007/0016029 A1 * | 1/2007 | Donaldson et al. ........... | 600/437 |
| 2007/0016066 A1 * | 1/2007 | Lee et al. ...................... | 600/463 |
| 2007/0049823 A1 * | 3/2007 | Li .................................. | 600/437 |
| 2009/0012398 A1 * | 1/2009 | Zhang et al. .................. | 600/453 |
| 2009/0030319 A1 * | 1/2009 | Zhang ........................... | 600/454 |
| 2009/0149759 A1 * | 6/2009 | Baba et al. .................... | 600/454 |
| 2009/0171204 A1 * | 7/2009 | Shin et al. ..................... | 600/441 |
| 2010/0106021 A1 * | 4/2010 | Li .................................. | 600/441 |
| 2012/0316444 A1 * | 12/2012 | Shim et al. .................... | 600/453 |

* cited by examiner

*Primary Examiner* — Sanjay Cattungal

(57) ABSTRACT

Gap filling is provided in spectral Doppler ultrasound. Due to the cyclical nature of the cardiac system, data likely to be similar to data that would have been acquired without interleaving is copied into the gap generated by interleaving. Acquired data associated with the gap, such as adjacent to the gap, is correlated with other acquired data. By identifying similar data, acquired data temporally related to the similar data as the gap associated data is temporally related to the gap is found. This found data is likely to be similar to data that would have been acquired during the gap. The gap is filled with a copy of this data.

23 Claims, 4 Drawing Sheets

GAP FILLING FOR SPECTRAL DOPPLER ULTRASOUND

BACKGROUND

The present invention relates to spectral Doppler ultrasound. Spectral Doppler ultrasound imaging provides an image of velocity (vertical axis) modulated by energy as a function of time (horizontal axis). These spectra may be used for studying fluid flow or tissue motion within a patient. By transmitting a plurality of pulses at a single gate location, a spectral Doppler response is generated with received echo signals. The frequency spectrum of the object's motion or flow for a single spatial region is estimated and displayed as a function of time. Flow or tissue deformation parameters may be derived from the acquisition.

To indicate the location of the gate, the spectral Doppler image is frequently provided with a B-mode and/or color flow mode (F-mode) image. These other images are acquired by ultrasound transmission. To provide this other information, the acquisition of data for spectral Doppler images may be interrupted. These interruptions result in gaps in the spectral Doppler data. When the spectral Doppler image is generated, gap artifacts result. FIG. 1 shows an example spectral Doppler image with a plurality of gap artifacts. The gap artifacts appear as vertical streaks.

BRIEF SUMMARY

By way of introduction, the preferred embodiments described below include methods, systems, computer readable media, and instructions for gap filling in spectral Doppler ultrasound. Due to the cyclical nature of the cardiac and respiratory systems, data likely to be similar to data that would have been acquired without gaps is copied into the gap generated by B-mode and/or color flow acquisitions. Acquired data associated with the gap, such as adjacent to the gap, is correlated with other acquired data. By identifying similar data, acquired data temporally related to the similar data as the gap associated data is temporally related to the gap is found. This found data is likely to be similar to data that would have been acquired during the gap. The gap is filled with a copy of this data.

In a first aspect, a method is provided for gap filling in spectral Doppler ultrasound. Spectral Doppler data representing a patient is acquired. A gap in the spectral Doppler data is identified. A first sub-set of the spectral Doppler data adjacent to the gap is selected. A second sub-set of the spectral Doppler data is determined based on correlation of the spectral Doppler data of the first sub-set with the spectral Doppler data. A third sub-set of the spectral Doppler data is selected relative to the second sub-set. The gap is filled with a copy of the spectral Doppler data of the third sub-set. A spectrum is estimated from the spectral Doppler data with the copy of the third sub-set in the gap. An image is displayed as a function of the spectrum.

In a second aspect, a non-transitory computer readable storage medium has stored therein data representing instructions executable by a programmed processor for gap filling in spectral Doppler ultrasound. The storage medium includes instructions for correlating samples from adjacent a gap in a sequence with samples spaced away from the gap, locating a group of samples spaced away from the gap as a function of the correlating, filling the gap in the sequence with the samples of the group, and estimating a spectrum from the samples including samples filling the gap.

In a third aspect, a system is provided for gap filling in spectral Doppler ultrasound. A memory is operable to store first data representing a sequence with a gap. A processor is configured to add second data into the gap by copying, into the gap, a first sub-set of the first data adjacent to a second sub-set of the first data that is similar to a third sub-set of the first data adjacent to the gap.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The gap in spectral Doppler data acquired in simultaneous Doppler mode is filled, reducing artifacts. Features in the time-domain or frequency-domain are used to identify an appropriate section of the other data to be used for filling the spectral gap. The corrected information may be used to improve the spectral Doppler display and/or audio.

Filling the gaps to reduce or remove gaps may improve work flow, providing diagnostic information with less distraction. Sonographers may be more likely to use simultaneous mode (e.g., both spectral Doppler and another mode (e.g., B-mode or F-mode)), providing additional diagnostic information.

Figure 2:
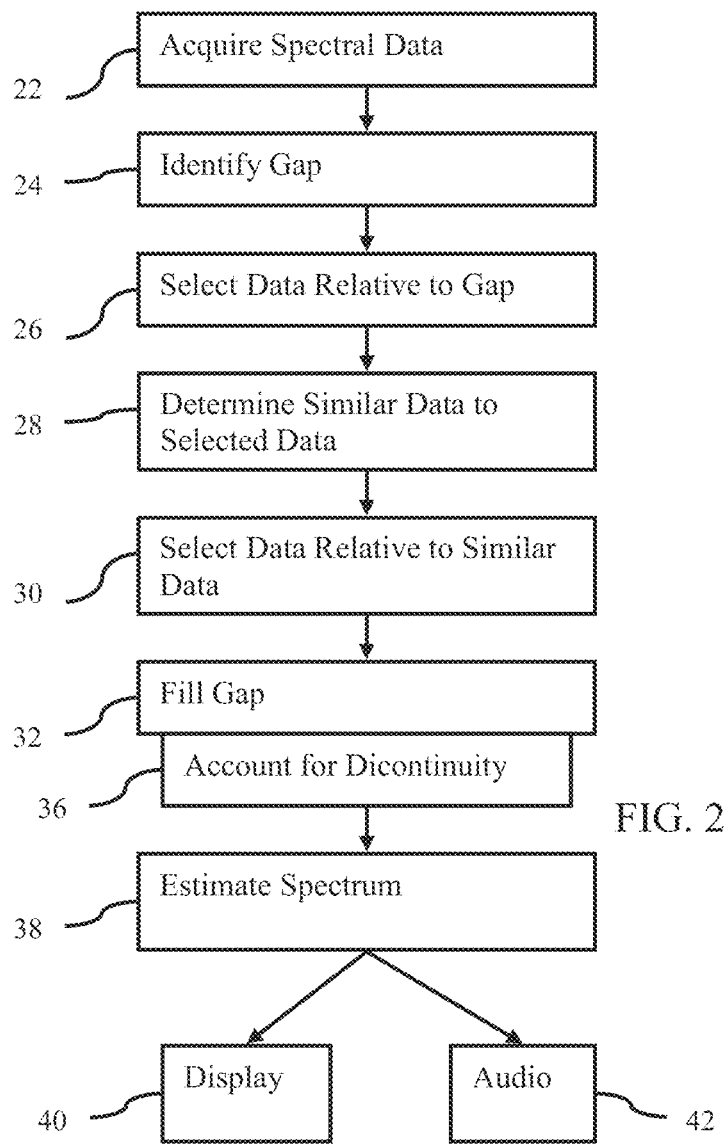
FIG. 2 is a flow chart diagram of one embodiment of a method for gap filling in spectral Doppler ultrasound.
Figure 7:
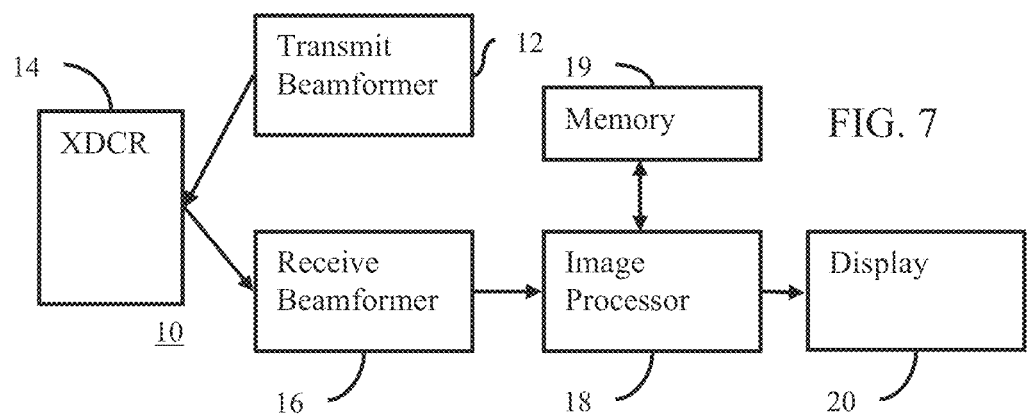
FIG. 7 is a block diagram of one embodiment of an ultrasound system for gap filling in spectral Doppler ultrasound.

FIG. 2 shows a method for gap filling in spectral Doppler ultrasound. The method is implemented on the system 10 of FIG. 7 or a different system. The acts are performed in the order shown, but other orders are possible. Additional, different, or fewer acts may be provided. For example, act 36 is not performed. As another example, one or both of acts 40 and 42 are not performed. In yet another example, acts associated with simultaneous imaging are included, such as transmissions, receiving, and processing for B-mode or F-mode interleaved with the acquisition of act 22.

In act 22, spectral Doppler data representing a patient is acquired. The spectral Doppler data is beamformed samples. The spectral Doppler data may be in the time-domain. Radio frequency or in-phase/quadrature (I/Q) samples output by the beamformer may be used to estimate the spectra, so may spectral Doppler data even if also available to use for other detection. In other embodiments, the spectral Doppler data is in the frequency domain. A fast Fourier transform (FFT) is applied to beamformed samples. The FFT bins values, providing spectral Doppler data in the frequency domain. In alternative embodiments, the spectral Doppler data is from other points in the processing, such as before beamformation or after binning.

The beamformed samples are obtained by transmitting beams. The transmit beams are repetitively transmitted to the same location or locations. In order to obtain samples for spectral analysis, the transmissions occur repetitively. The transmit beams are formed with any pulse repetition interval. The focal region of the transmit beam is at the gate location, but may be elsewhere.

Receive operation occurs in response to the transmitting. Signals from the gate location within the transmit beams are received. The signals received at each element in the receive aperture are combined or beamformed to generate a sample. Any scan sequence and/or pulse repetition frequency may be used.

Figure 3:
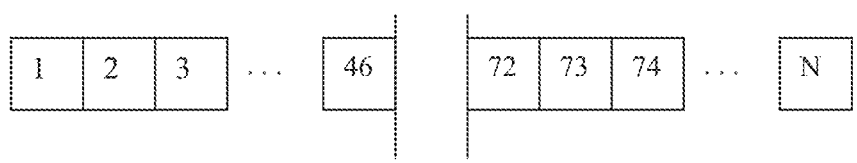
FIG. 3 is an illustration of one embodiment of spectral Doppler data in a sequence with a gap.

Each transmit and receive event generates a sample for the location. Samples for the same location are acquired over time. Samples are obtained over a period. By transmitting one or more beams from a transducer array, receiving responsive echoes, and then repeating, a series of samples are obtained for one or more locations. The series includes sufficient samples (e.g., 5 or more) for spectral analysis. The repetition allows reception of sufficient samples to perform spectral analysis. FIG. 3 shows an example where 46 samples are received in one period and samples 72-N are received in another period.

Other transmissions and receptions are performed. The transmissions and receptions for spectral Doppler may be interleaved with other transmissions and receptions. For example, transmissions and receptions to scan a two or three-dimensional region for B-mode or F-mode are performed. As another example, transmissions and receptions for M-mode imaging along a different scan line from the scan line for the spectral Doppler gate are performed. FIG. 3 shows a gap between samples 46 and 72. The gap corresponds to a time at which samples are acquired for other purposes than spectral Doppler. Other causes of the gap may exist.

Any interleaving pattern may be used. The interleaving allows an ongoing series to be acquired, such as over 0.05 seconds, for a given location. The scan then occurs for another region. Any period of continuously acquiring samples of spectral Doppler data and any period for acquiring samples for other purposes may be used. The periods may vary over time.

This interleaving repeats. Any repetition interval may be used. The interval is the same or varies over time. FIG. 3 shows one gap. This is representative. Other gaps may or may not be provided.

In act 24 of FIG. 2, the gap is identified. The gap is in the spectral Doppler data due to the interleaving or other cause. In the time domain, the samples are acquired with a time stamp. The time of acquisition is recorded or known. The time may be used to identify the gap. Where data is not available at the pulse repetition interval, a gap exists. In other embodiments, the gap is identified based on the schedule of beamformer operation. The interleaving of the scanning is known, so may be used to identify the gap.

In one embodiment, the gap, such as between samples 46 and 72 in FIG. 3, is identified in the time domain. The gap may be converted to the frequency domain to identify the gap associated with frequency-domain spectral Doppler data. Alternatively, the gap is determined in the frequency domain.

In act 26, a sub-set of the spectral Doppler data is selected. Any size sub-set may be used, such as four or more samples. The selected sub-set of samples is less than all of the samples. In one embodiment, at least ten samples are selected. The samples are contiguous or sequential samples. In other embodiments, every other (e.g., even samples from sample 30 to sample 46), other pattern (e.g., every third), or random selection may be used.

The sub-set is selected based on a relationship to the gap or other criteria. In one embodiment, the samples immediately adjacent to the gap are selected. In the example of FIG. 3, samples 37-46 are selected. There are no samples between the selected sub-set and the gap. In other embodiments, the samples of the sub-set are after the gap, but still immediately adjacent to the gap (e.g., samples 72-82). In yet other embodiments, the selected samples are spaced from the gap, such as selecting samples 33-40 in the example of FIG. 3. The same sub-set may include samples from both before and after the gap (e.g., selecting samples 34-46 and 72-79).

The selected sub-set is a kernel or group of spectral Doppler data. This kernel is used to match to other samples of the spectral Doppler data in act 28. Since the spectral Doppler data is cyclical, the occurrence of a similar sequence of samples as the selected sub-set is found. Another sub-set of samples is identified that matches the sub-set associated with the gap (e.g., adjacent to the gap or a known number of samples or time away from the gap).

The search for the similar sub-set is performed in a forward or backward direction in the time domain. Where data may not be acquired yet for searching forward in the time domain, then the search is performed with previously acquired data. In the example of FIG. 3, the search is of samples 1-36. Other size or number of samples may be searched.

The search may be along every sample, such as moving a window sized for the original sub-set from act 26. In other embodiments, other search patterns may be used. For example, the general period of the heart cycle is used. The search begins with samples likely acquired at a same phase in a pervious heart cycle or cycles. Coarse and fine searching may be used, such as searching by moving the window by more than one sample (e.g., step size of half the number of samples in the sub-set). Once the best match is found in the coarse search, the window may be moved by one sample at a time centered on the best match from the coarse search.

Any measure of similarly may be used. In one embodiment, a complex cross-correlation is performed. Since beamformed samples are complex values (e.g., I/O), complex cross-correlation is performed. A simple cross-correlation using I or Q data, a sum of absolute differences (SAD), taking a gradient and finding a matching slope, taking a second derivative and finding a matching inflection point, matching zero-crossings, or some combination of different calculations may be used in other embodiments. For frequency domain spectral Doppler data, a two-dimensional correlation may be used.

The measure is repeated for each position of a window. The selected sub-set is translated to different groups of samples and the similarity measured. The samples with the highest correlation are identified. The peak of the normalized complex cross-correlation result is used to locate the matching sub-set of the spectral Doppler data. In other embodiments, a sufficient correlation is identified. A threshold may be used. The samples first associated with a correlation above the threshold are selected.

Figure 4:
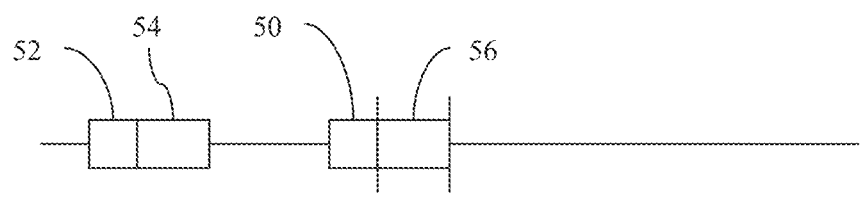
FIG. 4 is an illustration of different sub-sets of data used for gap filling according to one example.

In an example embodiment shown in FIG. 4, the sub-set 50 of data adjacent to the gap (e.g., between the vertical lines) is selected in act 26. Searching backwards in time, the sub-set 50 is translated to different times and correlation is performed. The correlation is repeated for other groups (e.g., moving window) of samples spaced away from the gap. A matching sub-set 52 of previous samples is determined to have the best or sufficient match to the initial sub-set 50 from adjacent to the gap.

In an alternative or additional embodiment, the Doppler data to fill the gap is identified using ECG timing information. When ECG timing information is available in conjunction with the acquired Doppler samples, then appropriate Doppler data for filling is identified based upon the ECG timing instead of using cross-correlation. For example, if a gap begins 47 psec after the peak of the R-wave in the ECG signal, than Doppler data previously acquired starting 47 psec after the peak of a previous R-wave can be used to fill in the gap. Both ECG and similarity based identification of the data for filling may be used. For example, ECG timing is used to facilitate cross-correlation searches and reduce the number of lags needed in the cross-correlation search.

In act 30 of FIG. 2, a sub-set of the spectral Doppler data is selected for filling the gap. In act 26, the sub-set is selected relative to the gap. This sub-set is matched to another sub-set in act 28. This other sub-set is similar to acquired data. The goal is to find a sub-set that would be similar to spectral Doppler data acquired in the gap if the data had been acquired. In act 30, the sub-set is selected relative to the matched sub-set based on the relationship between the original sub-set of act 26 and the gap.

In the example of FIG. 4, the original sub-set 50 is adjacent to the gap. This sub-set 50 is matched to the sub-set 52. Since the gap occurs after the original sub-set 50, the sub-set 54 is selected in act 30 as after the matched sub-set 52. If the original sub-set 50 were spaced from the gap, the same spacing in time or frequency is used to select the sub-set 54 relative to the matched sub-set 52. The relationship in time or frequency of the gap to the original sub-set 50 is applied to the matched sub-set 52 and the corresponding gap filling sub-set 54. Where the gap is immediately before or immediately after the original sub-set 50, the gap filling sub-set 54 is selected as immediately before or after the matching sub-set 52. Where the original sub-set 50 is selected to include samples before and after the gap, the gap filling sub-set 54 is selected to be between the samples of the matched sub-set 52.

The selected gap filling sub-set 54 is, like the matched sub-set 52, spaced away from the gap. The gap filling sub-set 54 includes the same or different number of samples as the matched sub-set 52. In one embodiment, the gap filling sub-set 54 includes a sufficient number of samples to fill the gap. The gap represents a period in which samples could have been obtained at the sampling frequency. The number of samples selected to be in the gap filling sub-set 54 is enough to fill the gap. In other embodiments, additional or fewer samples are selected.

In act 32 of FIG. 2, the gap in the sequence is filled. The samples from the gap filling sub-set 54 are placed in the gap as a sub-set 56 (see FIG. 4). Rather than create another gap, a copy of the samples is used to fill the gap. Due to the similarity and relative timing, the samples used to fill the gap are likely a continuation from the samples adjacent to the gap. Given the cyclical nature of spectral Doppler signals, the gap is filled with data likely emulating the samples that would have been acquired without interleaving.

Where the number of samples or period represented by the samples is the same as the number of missing samples or period of the gap, the copy 56 of the samples of the gap filling sub-set 54 fill the gap.

In other embodiments, any discontinuity is accounted for in act 36. If the number of samples is fewer than dictated by the length of the gap and the sample interval, then the discontinuity is dealt with by adding further samples, interpolating, extrapolating, or resampling. Alternatively, the spectrum is estimated with fewer samples, but enough to provide the spectrum.

There may be discontinuity at the end of the gap with or without sufficient samples. For example, the matched sub-set 52 has an ending sample value likely similar to the end of the original sub-set 50. As a result, the beginning of the gap filling sub-set 54 likely transitions well or matches the end of the original sub-set 50 at the beginning of the gap. The ending samples of the gap filling sub-set 54 and corresponding copy 56 may be match the post-gap data as well, especially where the samples after the gap are not used for correlating. Alternatively, the discontinuity may be at the beginning of the gap where the original sub-set for matching is formed from samples after the gap.

To account for discontinuity in the values of the copied samples at the beginning and/or ending of the gap, different processes may be used. The copied samples are aligned to the spectral Doppler data before or after the gap. In one embodiment, correlation is used to align. For example, complex cross-correlation is applied between a kernel from the copied data used to fill the gap and spectral Doppler data after and/or before the gap. Based on the complex cross-correlation result, data after and/or before gap is discarded to minimize the discontinuity of the data. Extra data is copied or the copied data is resampled to account for the discarded data. The data is better fit to the gap by aligning features in the gap data to the features in the pre and/or post gap Doppler data (e.g., aligning using cross-correlation).

In another embodiment, blending is used. The number of samples or period for gap filling extends beyond the gap. Samples for any amount of over lap may be copied. The overlapping samples are blended. For example, a weighted average is applied. The copied samples near the gap are more heavily weighted as well as the original or acquired samples further from the gap. For example and in reference to FIG. 3, the copied samples are provided for five samples over the gap (e.g., for samples 72-76). For sample 72, the copied sample is weighted more than original sample. For sample 76, the copied sample is weighted less than the original sample. Any transition function for the weighting may be used, such as a linear function representing a sloped line.

In another embodiments, features before and after the gap are used for correlation. The original sub-set includes samples from before and after the gap. The resulting matched data may have less discontinuity at the end or beginning of the gap than if only before or after samples were used. For a better match, the correlations may be performed independently. The data before is correlated separately from the data after. The result may be a sub-set of data to be copied that has more or fewer samples than would be provided in the gap. The copied samples may be resampled to fit the gap.

In act 38 of FIG. 2, a spectrum is estimated from the samples. The samples include acquired or original samples as well as one or more samples copied into the gap. A single spectrum is estimated. Alternatively, a sequence of spectra is estimated for multiple times. A spectrum or series of spectra are estimated from the received samples.

The spectra correspond to a period in which the samples were acquired. The time period may include any number of samples, such as estimating the spectrum with twenty samples. By repeating the estimation for different time periods, a sequence of spectra is estimated. Some samples may be used for different time periods, such as estimating each spectrum from a moving window of samples. Alternatively, samples are used once. The step size of the window may be any number of samples, such as one or more samples for each estimation. Different spectra may be estimated for the same spatial location at different times corresponding to different periods of acquisition.

Figure 5:
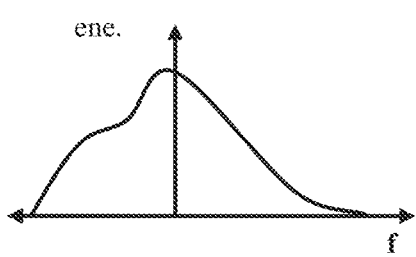
FIG. 5 is a graphical representation of an example spectrum.
Figure 6:
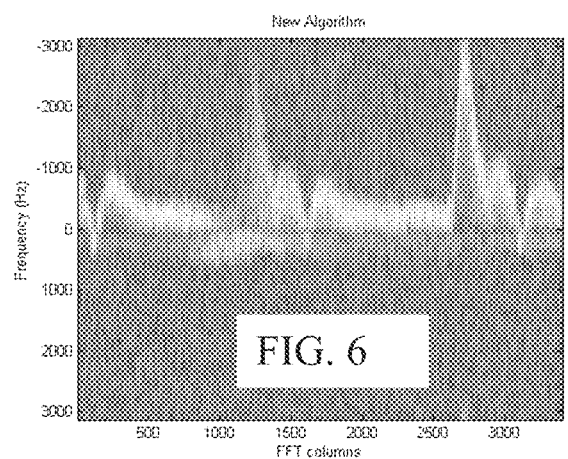
FIG. 6 is an example medical image of a spectral Doppler display after gap filling.

The spectra are estimated by applying a Fourier transform, wavelet transform or Wigner-Ville distribution to the ultrasound samples. FIG. 5 shows a spectrum. Any transform may be applied to determine the spectrum. The spectra represent energy as a function of frequency. FIG. 6 shows a spectral strip of spectra for a same location over time.

Where additional gaps occur, the identification of act 24, the selection of act 26, the determination of act 28, the selection of act 30, and the filling of act 32 are repeated. The process is performed for each of the gaps. A given spectrum may be estimated from samples filled into none, one, or more gaps. A sequence of spectra may be estimated from samples filled into none, one, or more gaps.

In act 40, an image is displayed. The image is a function of the estimated spectrum or spectra. For example, a maximum velocity is determined from the spectrum. Text or other indication of the velocity may be output. As another example, the spectrum is used as part of a display of the spectrum, such as a graph represented in FIG. 5. In yet another example, the spectrum is used as part of a spectral Doppler display or spectral strip display. The spectral strip shows the frequency modulated by energy as a function of time. Any now known or later developed spectral strip mapping may be used, such as gray scale mapping with the intensity representing energy. Filtering may be applied to smooth the spectrum. Characteristics of the spectral strip may be determined and displayed, such as graphically tracking a maximum velocity as a function of time in the spectral strip.

Figure 1:
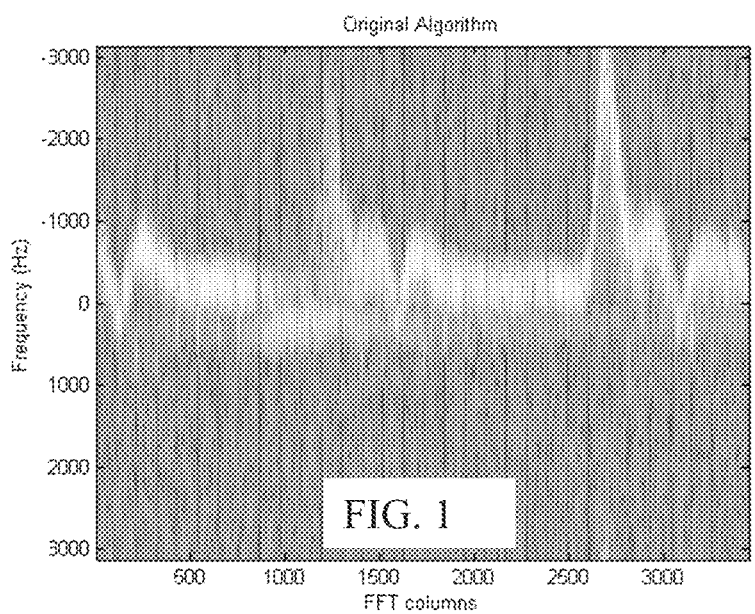
FIG. 1 is an example medical image of a spectral Doppler display with streak artifacts.

FIG. 6 shows a spectral strip display using the samples used for FIG. 1, but with the gaps filled. The streak or gap artifacts are no longer or less visible. The copied samples fill the gaps and are used to estimate one or more spectra in the ongoing spectral strip display. Due to the filling, streak artifacts are reduced and the signal-to-noise ratio may be improved. Since data from the patient is identified with correlation, the filling may more accurately represent the patient than other gap filling.

In act 42, the spectra are output as audio. The Doppler shift frequency is in the audio range. The spectral information may be provided to a speaker. The speaker generates audio based on the input spectra. The audio may have improved characteristics due to the gap filling.

FIG. 8 shows a system 10 for gap filling in spectral Doppler ultrasound. The system 10 is a medical diagnostic ultrasound imaging system, but other imaging systems may be used, such as a workstation. The system 10 estimates spectra during simultaneous Doppler imaging.

The system 10 includes a transmit beamformer 12, a transducer 14, a receive beamformer 16, an image processor 18, a display 20, and a memory 22. Additional, different or fewer components may be provided, such as the system 10 without the front-end beamformers 12, 16 and transducer 14 or the system 10 with a scan converter.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit beamformer 12 is shown separate from the receive beamformer 16. Alternatively, the transmit and receive beamformers 12, 16 may be provided with some or all components in common. Operating together or alone, the transmit and receive beamformers 12, 16 form beams of acoustic energy for scanning a one, two, or three-dimensional region. Vector®, sector, linear or other scan formats may be used. For spectral Doppler imaging, pulse wave Doppler scanning is provided along one or more scan lines.

The transmit beamformer 12 is a processor, delay, filter, waveform generator, memory, phase rotator, digital-to-analog converter, amplifier, combinations thereof, or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. In other embodiments, the transmit beamformer 12 includes switching pulsers or waveform memories storing the waveforms to be transmitted. Other transmit beamformers 12 may be used.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, coding, and combinations thereof.

The transmit beamformer 12 is operable to transmit one or more transmit beams of ultrasound energy substantially simultaneously. A transmit beam originates from the transducer 14 at a location in the transmit aperture. The transmit beam is formed along a scan line at any desired angle. The acoustic energy is focused at a point along the scan line, but multiple points, line focus, no focus, or other spread may be used.

The receive beamformer 16 is a preamplifier, filter, phase rotator, delay, summer, base band filter, processor, buffers, memory, combinations thereof, or other now known or later developed receive beamformer component. Analog or digital receive beamformers capable of receiving one or more beams in response to a transmit event may be used. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay for applying apodization amplification. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. The summer sums the relatively delayed and apodized channel information together to form a beam. In one embodiment, the beamform summer is operable to sum in-phase and quadrature channel data in a complex manner such that phase information is maintained for the formed beam. Alternatively, the beamform summer sums data amplitudes or intensities without maintaining the phase information. Other receive beamformation may be provided, such as with demodulation to an intermediate frequency band and/or analog-to-digital conversion at a different part of the channel.

Beamforming parameters including a receive aperture (e.g., the number of elements and which elements used for receive processing), the apodization profile, a delay profile, a phase profile, imaging frequency, inverse coding, and combinations thereof are applied to the receive signals for receive beamforming. For example, relative delays and amplitudes or apodization focus the acoustic energy along one or more scan lines. A control processor controls the various beamforming parameters for receive beamformation.

Acoustic echoes are received by the transducer 14 in response to the transmit beam. The echoes are converted into electrical signals by the transducer 14, and the receive beamformer 16 forms the receive samples from the electrical signals. The receive samples represent a gate location along a scan line. The receive beamformer 16 outputs data representing the acoustic response from the location of the spectral gate.

The image processor 18 includes a spectral Doppler processor and/or imaging detectors. A separate control processor is provided as part of the image processor 18. Alternatively, the processor or processors used for estimation or detection control the imaging and/or system 10. The image processor 18 is a general processor, control processor, digital signal processor, application specific integrated circuit, field programmable gate array, analog circuit, digital circuit, combinations thereof or other now known or later developed device for processing.

In one embodiment, the image processor 18 is a digital signal processor or other device for applying a transform to the receive beam data. A sequence of transmit and receive events is performed over a period. A buffer or the memory 22 stores the receive beamformed data from each transmit and receive event. Any pulse repetition interval may be used for the transmit beams. Any number of transmit and receive events may be used for determining a spectrum, such as three or more. The image processor 20 is operable to estimate a spectrum. By applying a discrete or fast Fourier transform, or other transform, to the ultrasound samples for the same spatial location, the spectrum representing response from the location is determined. Samples in the frequency domain are provided by the transform. A histogram or data representing the energy level at different frequencies for the period of time to acquire the beamformed samples is obtained.

By repeating the process, the image processor 20 may obtain different spectra for a given location at different times. Overlapping data may be used, such as calculating each spectrum with a moving window of selected ultrasound samples. Alternatively, each ultrasound sample is used for a single period and spectrum.

The image processor 18 is configured by hardware and/or software to fill any gaps in the samples. The image processor 18 adds data into the gap by copying from other data. The data to be copied is found based on correlation with data adjacent to or with a known relationship relative to the gap. By finding the similar data, the image processor 18 determines what data to use for filling the gap.

The image processor 18 generates display values as a function of the spectra. Display values include intensity or other values to be converted for display, values provided to the display 20 (e.g., red, green, blue values), or analog values generated to operate the display 20. The display values may indicate intensity, hue, color, brightness, or other pixel characteristic. For example, the color is assigned as a function of one characteristic of a spectrum and the brightness is a function of another spectrum characteristic or other information. The display values are generated for a spectral strip display, a graph of the spectrum, or text.

The image processor 18 may include a B-mode detector for determining intensity and/or a color Doppler detector for determining average velocity, variance, and/or energy. One or more filters, such as clutter, spatial or temporal filters may be provided. The detector outputs incoherent image data. Additional processes, such as filtering, interpolation, and/or scan conversion, may be provided by the image processor 18.

The display 18 is a CRT, monitor, LCD, plasma screen, projector or other now known or later developed display for displaying an image responsive to the display value. For a black and white spectral Doppler image, a range of velocities with each velocity modulated as a function of energy is provided as a function of time. The spectrum indicates the velocity and energy information for a given time. The intensity of a given pixel or pixel region represents energy where velocity is provided on the vertical scale and time provided on the horizontal scale. Other image configurations may be provided, including colorized spectral Doppler images.

The memory 22 stores buffered data, such as ultrasound samples for spectrum estimation. Spectral Doppler samples in the time domain or frequency domain are stored. The stored data represents a sequence with a gap, data to fill the gap, and/or the sequence with the gap filled. The memory 22 may store display values or images, such as a CINE memory.

In one embodiment, the memory 22 is a non-transitory computer readable storage medium having stored therein data representing instructions executable by the programmed processor 18 for gap filling in spectral Doppler ultrasound. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for gap filling in spectral Doppler ultrasound, the method comprising:
   acquiring spectral Doppler data representing a patient;
   identifying a gap in the spectral Doppler data;
   selecting a first sub-set of the spectral Doppler data adjacent to the gap;
   determining a second sub-set of the spectral Doppler data based on correlation of the spectral Doppler data of the first sub-set with the spectral Doppler data;
   selecting a third sub-set of the spectral Doppler data, the third sub-set selected relative in time to the second sub-set;
   filling the gap with a copy of the spectral Doppler data of the third sub-set;
   estimating a spectrum from the spectral Doppler data with the copy of the third sub-set in the gap; and
   displaying an image as a function of the spectrum.

2. The method of claim 1 wherein acquiring comprises acquiring the spectral Doppler data as a sequence of beamformed samples in a time domain.

3. The method of claim 1 wherein acquiring comprises acquiring the spectral Doppler data as frequency domain data.

4. The method of claim 1 wherein identifying the gap comprises identifying interleaving of scanning.

5. The method of claim 1 wherein selecting comprises selecting the first sub-set as a plurality of samples immediately before or immediately after the gap.

6. The method of claim 1 wherein determining comprises determining the second sub-set as having a highest complex cross correlation with the spectral Doppler data of the first sub-set within a period from the first sub-set.

7. The method of claim 1 wherein selecting the third sub-set comprises selecting the third sub-set as immediately before or immediately after the second sub-set.

8. The method of claim 1 wherein selecting the third sub-set comprises selecting the third sub-set as being for a period based on the gap.

9. The method of claim 1 wherein estimating the spectrum is performed as part of estimating a series of spectra for a location over time, and wherein displaying comprises displaying a spectral Doppler image.

10. The method of claim 1 further comprising repeating identifying, selecting the first sub-set, determining, selecting the third sub-set, filling, and estimating for each of different gaps.

11. The method of claim 1 further comprising:
    aligning the copy to the spectral Doppler data after the gap with correlation.

12. The method of claim 1 wherein the third sub-set is for a longer period than the gap;
    further comprising:
    blending some of the spectral Doppler data of the third sub-set with spectral Doppler data after the gap.

13. The method of claim 1 wherein selecting the first sub-set comprises selecting the spectral Doppler data from before and after the gap, and wherein selecting the third sub-set comprises selecting the third sub-set as spectral Doppler data between the spectral Doppler data of the second sub-set.

14. The method of claim 13 further comprising:
    resampling the spectral Doppler data of the third sub-set based on a size of the gap.

15. The method of claim 1 wherein determining comprises:
    identifying ECG timing of the gap relative to a heart cycle; and
    determining the second sub-set with a correlation search region being based on the ECG timing.

16. In a non-transitory computer readable storage medium having stored therein data representing instructions executable by a programmed processor for gap filling in spectral Doppler ultrasound, the storage medium comprising instructions for:
    correlating samples in a first sub-set adjacent a gap in a sequence with a second sub-set of samples spaced away from the gap;
    locating a group of samples as a third sub-set spaced away from the gap as a function of the correlating;
    filling the gap in the sequence with the samples of the group of the third sub-set; and
    estimating a spectrum from the samples including samples filling the gap.

17. The non-transitory computer readable storage medium of claim 16 wherein correlating comprises complex cross-correlating the samples of the first sub-set with the samples of the second sub-set.

18. The non-transitory computer readable storage medium of claim 16 wherein locating comprises locating the samples of the second sub-set with a highest correlation with the samples of the first sub-set from adjacent the gap, and wherein filling the gap comprises copying the group of samples of the third sub-set into the sequence at the gap, the samples of the third sub-set being adjacent to the samples of the second sub-set as the samples of the first sub-set are adjacent to the gap.

19. The non-transitory computer readable storage medium of claim 16 wherein filling comprises accounting for a discontinuity at an end of the gap with the group of samples of the third sub-set.

20. The non-transitory computer readable storage medium of claim 16 wherein correlating comprises correlating in a time domain or in a frequency domain.

21. The non-transitory computer readable storage medium of claim 16 further comprising outputting audio signals as function of the spectrum.

22. A system for gap filling in spectral Doppler ultrasound, the system comprising:
    a memory operable to store first data representing a sequence with a gap, the first data comprising beamformed samples; and
    a processor configured to select a third sub-set of first data adjacent to the gap, determine a second sub-set of the first data based on similarity with the third-sub set, select a first sub-set of the first data relative in time to the second sub-set, add the first sub-set of the first data into the gap by copying into the gap and estimating a spectrum from the spectral Doppler data with the copy of the first subset.

23. In a non-transitory computer readable storage medium having stored therein data representing instructions executable by a programmed processor for gap filling in spectral Doppler ultrasound, the storage medium comprising instructions for:
    determining a time of a gap relative to a heart cycle;
    locating a group of samples spaced away from the gap as a function of correlation of a sub-set of samples adjacent the gap in time with a sub-set of samples spaced from the gap in time, the group of samples located as adjacent in time to the sub-set of samples spaced from the gap in time;
    filling the gap in the sequence with the samples of the group; and estimating a spectrum from the samples including samples filling the gap.

* * * * *